(12) United States Patent
Sneed

(10) Patent No.: US 6,348,506 B2
(45) Date of Patent: Feb. 19, 2002

(54) TREATMENT OF FIBROMYALGIA WITH UBIQUINONE 10 AND SUCCINIC ACID

(76) Inventor: Paul A. Sneed, Route 3, Box 08 C5, Cisco, TX (US) 76437

(*) Notice: Subject to any disclaimer, the term of this patent is extended or adjusted under 35 U.S.C. 154(b) by 0 days.

(21) Appl. No.: 09/780,299

(22) Filed: Feb. 9, 2001

Related U.S. Application Data

(60) Provisional application No. 60/181,314, filed on Feb. 9, 2000.

(51) Int. Cl.[7] .......................... A61K 31/12; A61K 31/19
(52) U.S. Cl. ..................... 514/678; 514/557; 514/675
(58) Field of Search ....................... 514/678, 557, 514/675

(56) References Cited

U.S. PATENT DOCUMENTS

| 5,082,650 | A | * | 1/1992 | Folker et al. |
| 5,316,765 | A | * | 5/1994 | Folkers et al. |
| 5,891,469 | A | * | 4/1999 | Amselem |
| 5,902,831 | A | * | 5/1999 | Hollan |
| 5,958,746 | A | * | 9/1999 | Hillman et al. |

OTHER PUBLICATIONS

Lindh et al., Plasma nutrients in joint and muscle pain . . . , Journal of nutritional and environmental medicine, 1997, col. 7, pp. 15–26.*

* cited by examiner

Primary Examiner—William R. A. Jarvis
Assistant Examiner—Vickie Kim
(74) Attorney, Agent, or Firm—Barnes & Thornburg

(57) ABSTRACT

A method is described for using a combination of ubiquinone 10 and succinic acid in the treatment of human patients afflicted with fibromyalgia to alleviate one or more symptoms associated with that disease state. Fibromyalgia positive patients treated buccally, sublingually or by oral ingestion administration of ubiquinone 10 and succinic acid enjoy a reduction in clinical symptoms of the disease.

12 Claims, No Drawings

TREATMENT OF FIBROMYALGIA WITH UBIQUINONE 10 AND SUCCINIC ACID

CROSS REFERENCE TO RELATED APPLICATIONS

This application claims priority under 35 U.S.C. § 119(e) to U.S. Provisional Application No. 60/181,314, filed Feb. 9, 2000, which is expressly incorporated by reference herein.

FIELD OF INVENTION

The present invention relates to a composition and method for treatment of patients afflicted with fibromyalgia. More particularly, this invention is directed to a composition and method for relieving symptoms associated with fibromyalgia in human patients by administering a combination of ubiquinone 10 and succinic acid.

BACKGROUND AND SUMMARY OF THE INVENTION

Fibromyalgia is a common disabling disorder characterized by chronic musculoskeletal aches and pain, stiffness, and sleep abnormalities including diminished stage four sleep. Examination of affected patients reveals increased tenderness at muscle and tendon insertion sites, known as "tender points." Fibromyalgia patients experience severe morning stiffness and a generalized decreased of overall physical function, and they are often prone to headaches, memory and concentration problems, dizziness, numbness and tingling, and crampy abdominal or pelvic pain. Fibromyalgia affects 2–4% of the population and is most frequently found in women between 20 and 50 years old, although it can also affect men, the elderly and minors.

Diagnosis of fibromyalgia is often overlooked due to the general nature of the symptoms and the lack of diagnostic lab or x-ray abnormalities. The disorder is often concomitant with, masked by or confused with other diseases such as rheumatoid arthritis, chronic fatigue syndrome or irritable bowl syndrome. However, chronic fatigue syndrome (CFS) can be distinguished from fibromyalgia because patients with CFS are likely to have symptoms of viral illnesses such as fever, sore throat, and lymph node pain. A physician can positively diagnose fibromyalgia syndrome by finding the symptoms of musculoskeletal pain throughout the body and pain at more than 11 of 18 symmetrically distributed characteristic "tender points" when a finger pressure of about 4 kg is applied to the area, which test is known as the "tender point index," or when tender points are detected with dolorimetry.

Currently the best treatment available for fibromyalgia consists of a combination of analgesics, sleep aids, exercise programs emphasizing stretching and cardiovascular fitness, relaxation techniques and other measures to reduce muscle tension, and educational programs to reduce emotional and physical stress. Numerous pharmaceutical regimens have been tried including treatment with serotonin modulators and antisera to endogenous psychoactive agents. Therapeutic response can be assessed by the reduction of pain in the tender point index and improvement in several generalized criteria such as physical function, stiffness, fatigue, depression, tenseness, etc. Responses to these various therapies have proven variable within a patient pool and have rarely exceeded modest relief of some symptoms. Often, initial therapeutic gains are temporary with the long term outcome marginally if at all distinguishable from placebo results.

Ubiquinone 10 and succinic acid are physiological substances present in all living cells. Succinic acid is oxidized to fumarate as one of the nine steps in the citric acid cycle, and oxidation of succinic acid results in the release of two electrons which are transferred to flavin adenine dinucleotide (FAD) to generate the reduced form of the molecule, $FADH_2$. Electrons are then sequentially transferred between various flavin-linked dehydrogenases in the electron transport pathway localized on the inner mitochondrial membrane. Electron transport results in proton transport across the mitochondrial membrane and powers ATP synthesis through coupling with the oxidative phosphorylation pathway.

Ubiquinone 10 (CoQ10) is a lipophilic electron carrier that transports electrons between the various flavin-linked dehydrogenases in the electron transport pathway through reduction and oxidation of CoQ10. CoQ10 contains ten isoprene units in the multiprenyl side chain of the molecule which renders CoQ10 lipophilic and facilitates interaction of the molecule with the inner mitochondrial membrane where the components of the electron transfer chain are located. CoQ10 complexes with succinic acid and succinate dehydrogenase, the enzyme responsible for catalyzing the oxidation of succinic acid to fumarate, and acts as an electron carrier to facilitate the transfer of electrons from succinic acid to FAD. CoQ10 is widely distributed in tissues and may also act an antioxidant for such endogenous molecules as low density lipoproteins.

There exists a significant need for more effective therapy for patients afflicted with fibromyalgia. The present invention is directed to a method for treating a human patient suffering from fibromyalgia to produce a therapeutic response in the patient. The method comprises the step of administering to the patient ubiquinone 10 and succinic acid each at a dose of about 5 to about 500 mg/70 kg patient. In one embodiment of the invention the ubiquinone 10 and the succinic acid are each administered at a dose of about 50 to about 400 mg/70 kg patient and are administered by oral ingestion, bucally, sublingually, or parenterally. In another embodiment of the invention the ubiquinone 10 and succinic acid are each administered at a dose of about 50 to about 200 mg/70 kg patient. The ubiquinone 10 and succinic acid may be administered in a solid, liquid, or saliva-soluble dosage form, such as a lozenge. The daily doses can be divided into multiple doses administered one or more times per day.

In another embodiment, the invention provides a pharmaceutical composition comprising therapeutically effective amounts of ubiquinone 10 and succinic acid as the active ingredients, and a pharmaceutically acceptable carrier therefor. The pharmaceutical composition can be in the form of a liquid solution, a capsule, a caplet, a tablet, a gel-seal, or a lozenge and can be adapted for oral or parenteral administration.

DETAILED DESCRIPTION OF THE INVENTION

The present invention provides a method for treating a human patient suffering from fibromyalgia to produce a therapeutic response in the patient. The method comprises the step of administering to the patient ubiquinone 10 and succinic acid each at a dose of about 5 to about 500 mg/70 kg patient. The ubiquinone 10 and succinic acid may be administered by oral ingestion, bucally, sublingually, or parenterally and may be administered in a pharmaceutically acceptable solid, liquid, or saliva-soluble dosage form, such as a lozenge. In a preferred embodiment, the ubiquinone 10 and succinic acid are taken with food. In accordance with the present invention, there is also provided a pharmaceutical composition comprising therapeutically effective amounts of ubiquinone 10 and succinic acid as the active ingredients, and a pharmaceutically acceptable carrier therefor. The pharmaceutical composition may be in the form of a suspension, a capsule or caplet, a tablet, a gel-seal, or a lozenge, and may be adapted for oral or parenteral administration.

Succinic acid is an intermediate in the citric acid cycle and, thus, is a physiological compound found in living cells. Succinic acid is oxidized to form fumarate as a step in the citric acid cycle and, upon oxidation of succinic acid, two electrons are released and are transferred to FAD to generate the reduced form of the molecule, $FADH_2$, as the first step in the electron transport pathway. Electrons are then sequentially transferred between various flavin-linked dehydrogenases in the electron transport pathway resulting in the generation of ATP through coupling with oxidative phosphorylation. Ubiquinone 10 is an electron carrier that facilitates transport of electrons between the various flavin-linked dehydrogenases in the electron transport pathway, and complexes with succinic acid and succinate dehydrogenase to facilitate the transfer of electrons generated by oxidation of succinic acid to FAD. Methods of producing ubiquinone 10 are well known in the art and one such method is disclosed in U.S. Pat. No. 4,070,244 incorporated herein by reference in its entirety. Succinic acid is commercially available from Aldrich Chemical Company, Milwaukee, Wis.

In accordance with the present invention, a method is provided for treating a human patient suffering from fibromyalgia to produce a therapeutic response. A "therapeutic response" is a response to treatment with ubiquinone 10 and succinic acid in which one or more of the clinical symptoms of fibromyalgia in a patient with the disease are prevented, reduced, or stabilized whether such improved patient condition is permanent or temporary. Ubiquinone 10 and succinic acid may also be used in combination for the treatment of other disease states including such diseases as adult onset diabetes, autoimmune disorders such as lupus erythematosus, and chronic fatigue syndrome. A "therapeutic response" to treatment with ubiquinone 10 and succinic acid for any of these disease states is also a response in which one or more of the clinical symptoms of disease are prevented, reduced, or stabilized whether such improved patient condition is permanent or temporary. The term "succinic acid" as used herein to claim and describe the method and composition of the present invention will be understood to include pharmaceutically acceptable salts of succinic acid, succinic acid anhydride and succinic acid esters which, upon administration to a patient, can serve as a source of succiniate in vivo via in vivo hydrolysis or neutralization under physiological conditions.

In one embodiment of this invention, the method for treating a patient suffering from fibromyalgia to produce a therapeutic response comprises the step of administering ubiquinone 10 and succinic acid by oral ingestion each at a dose of about 5 to about 500 mg/70 kg patient. In another embodiment, the compounds are administered at a dose of about 50 to about 400 mg/70 kg patient. In an alternate embodiment, the compounds are administered at a dose of about 50 to about 200 mg/70 kg patient for relief of one or more symptoms of fibromyalgia. The daily doses of ubiquinone 10 and succinic acid can be administered as single daily doses or in more than one dose per day until the patient's symptoms of fibromyalgia have subsided. The ubiquinone 10 and succinic acid may also be administered in different weight ratios in single daily doses or in a multi-dose regimen, and, preferably, are taken with food. In a preferred embodiment, for example, the ubiquinone 10 is administered with food at about 100 mg/70 kg patient per dose and the succinic acid at about 400 mg/70 kg patient per dose in single or in two daily doses. In another preferred embodiment, the ubiquinone 10 is administered at about 25 mg/70 kg patient per dose and the succinic acid at about 100 mg per dose and the compounds are taken with food 2–4 times daily with food to achieve daily ubiquinone 10 and succinic acid doses of 50–100 mg/70 kg patient and 200–400 mg/70 kg patient, respectively. In yet another preferred embodiment these same ubiquinone 10 and Succinic acid doses are administered twice daily with food to achieve daily doses of 50 and 200 mg/70 kg patient, respectively.

Oral ingestion may be achieved by the use of such dosage forms of ubiquinone 10 and succinic acid as syrups, sprays, or other liquid dosage forms, a gel-seal, or a capsule or caplet. Buccal and sublingual administration comprises contacting the oral and pharyngeal mucosa of the patient with the dose of ubiquinone 10 and succinic acid either in a pharmaceutically acceptable liquid dosage form, such as a syrup or a spray, or in a saliva-soluble dosage form which is held in the patient's mouth to form a saliva solution of ubiquinone 10 and succinic acid in contact with the oral and pharyngeal mucosa. Exemplary of saliva-soluble dosage forms are lozenges, tablets, and the like. Parenteral administration can be accomplished by injection of a liquid dosage form of ubiquinone 10 and succinic acid, such as by injection of a solution of the two compounds dissolved in a pharmaceutically acceptable buffer. Such parenteral administration may be intradermal, subcutaneous, intramuscular, intraperitoneal, or intravenous.

The ubiquinone 10 and succinic acid intended for buccal or sublingual administration in accordance with the present invention is administered to the patient in a dosage form adapted to promote contact of the administered ubiquinone 10 and succinic acid with the patient's oral and pharyngeal mucosa. Thus, the dosage form can be in the form of a liquid solution such as a syrup, spray, or other liquid dosage form to be administered and used by the patient in a manner which promotes contact of the ubiquinone 10 and succinic acid components with oral mucosal tissues, for example, by holding the ubiquinone 10 and succinic acid solution in the mouth for up to one or two minutes. Alternatively, the ubiquinone 10 and succinic acid can be administered by oral ingestion wherein the compounds are formulated into a syrup to be swallowed by the patient and not held in the mouth. Syrups for either use may be flavored or unflavored and may be formulated using a buffered aqueous solution of ubiquinone 10 and succinic acid as a base with added caloric or non-caloric sweeteners, flavor oils and pharmaceutically acceptable surfactant/dispersants. Other liquid dosage forms, including solutions or sprays containing ubiquinone 10 and succinic acid, can be prepared in a similar manner and can be administered buccally, sublingually, or by oral ingestion.

Preferably, the ubiquinone 10 and succinic acid for buccal/sublingual administration in the present invention is formulated into a solid dosage form, such as a lozenge or a tablet. This formulation preferably contains ubiquinone 10, succinic acid and a saliva-soluble carrier and may optionally contain desirable excipients, such as buffers, or tableting aids. The solid dosage form is formulated to dissolve, when held in a patient's mouth, to form a saliva solution of the ubiquinone 10 and succinic acid to promote contact of the compounds with the oral and pharyngeal mucosa.

In one embodiment, the solid dosage form is in the form of a lozenge adapted to be dissolved upon contact with saliva in the mouth, with or without the assistance of chewing, to form a saliva solution of ubiquinone and succinic acid. In this embodiment, lozenges are formulated to provide about 5 to about 500 mg/70 kg patient of ubiquinone 10 and succinic acid, preferably about 50 to about 400 mg/70 kg patient. In another preferred embodiment, about 50 to about 200 mg/70 kg patient of ubiquinone 10 and succinic acid is provided upon dissolution of the dosage form in saliva in the mouth. Ubiquinone 10 and succinic acid are preferably taken with food.

Lozenges for use in accordance with this invention can be prepared, for example, by art-recognized techniques for forming compressed tablets where the ubiquinone 10 and succinic acid is dispersed on a compressible solid carrier, optionally combined with any appropriate tableting aids such as a lubricant (e.g., magnesium-stearate) and is compressed into tablets. The solid carrier component for such tableting formulations can be a saliva-soluble solid, such as a cold water-soluble starch or a monosaccharide or disaccharide, so that the lozenge will readily dissolve in the mouth to release the contained ubiquinone 10 and succinic acid in saliva solution for contact with and absorption by the oral/pharyngeal mucosa when the lozenge is held in the mouth. The pH of the above-described formulations can range from about 4 to about 8.5. Lozenges for use in accordance with the present invention can also be prepared utilizing other art-recognized solid unitary dosage formulation techniques.

Tablets for use in accordance with this invention can be prepared in a manner similar to that described for preparation of lozenges or by other art-recognized techniques for forming compressed tablets such as chewable vitamins. Suitable solid carrier components for tableting include manitol, microcrystalline cellulose, carboxymethyl cellulose, and dibasic calcium phosphate.

Solid dosage forms for oral ingestion administration include such dosage forms as caplets, capsules, and gel-seals. Such solid dosage forms can be prepared using standard tableting protocols and excipients to provide ubiquinone 10 and succinic acid-containing capsules, caplets, or gel-seals. Any of the solid dosage forms for use in accordance with the invention, including lozenges and tablets, may be in a form adapted for sustained release of the ubiquinone 10 and succinic acid.

In accordance with one embodiment of the present invention a pharmaceutical composition is provided comprising therapeutically effective amounts of ubiquinone 10 and succinic acid, and a pharmaceutically acceptable carrier therefor. "Therapeutically effective amounts" of ubiquinone 10 and succinic acid are amounts of the compounds which prevent, reduce, or stabilize one or more of the clinical symptoms of fibromyalgia in a patient suffering from the disease whether such improved patient condition is permanent or temporary. In one embodiment the pharmaceutical composition comprises about 5 to about 500 mg/70 kg patient of ubiquinone 10 and succinic acid per dose in combination with a pharmaceutically acceptable carrier. A preferred pharmaceutical composition comprises about 50 to about 400 mg/70 kg patient per dose of each of the two compounds in combination with the carrier. In another preferred embodiment, the pharmaceutical composition comprises about 50 to about 200 mg/70 kg patient of ubiquinone 10 and succinic acid per dose in combination with the pharmaceutically acceptable carrier. The ubiquinone 10 and succinic acid may be present in the pharmaceutical composition at different weight ratios. Most preferably, the pharmaceutical composition comprises about 100 mg/70 kg patient per dose of ubiquinone 10 and 400 mg/70 kg patient per dose of succinic acid. In another preferred embodiment, the pharmaceutical comprises about 25 mg/70 kg patient per dose of ubiquinone 10 and 100 mg per dose of succinic acid administered 2–4 times daily with food to achieve daily ubiquinone 10 and succinic acid doses of 50–100 mg/70 kg patient and 200–400 mg/70 kg patient, respectively. In yet another preferred embodiment the pharmaceutical composition comprises about 50 mg/70 kg patient per dose of ubiquinone 10 and 200 mg/70 kg patient per dose of succinic acid administered twice daily with food to achieve daily doses of 100 and 400 mg/70 kg patient, respectively.

A "pharmaceutical acceptable carrier" for use in accordance with the invention is compatible with other reagents in the pharmaceutical composition and is not deleterious to the patient. The pharmaceutically acceptable carrier formulations for pharmaceutical compositions adapted for oral ingestion or buccal/sublingual administration including lozenges, tablets, capsules, caplets, gel-seals, and liquid dosage forms, including syrups, sprays, and other liquid dosage forms, have been described above. Ubiquinone 10 and succinic acid can also be adapted for parenteral administration in accordance with this invention using a pharmaceutical acceptable carrier adapted for use in a liquid dose form. Thus, ubiquinone 10 and succinic acid can be administered dissolved in a buffered aqueous solution typically containing a stabilizing amount (1–5% by weight) of albumin or blood serum. Such a liquid solution of ubiquinone 10 and succinic acid may be in the form of a clarified solution or a suspension. Exemplary of a buffered solution suitable as a carrier of ubiquinone 10 and succinic acid administered parenterally in accordance with this invention is phosphate buffered saline prepared as follows:

A concentrated (20×) solution of phosphate buffered saline (PBS) is prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The solution is sterilized by autoclaving at 15 pounds of pressure for 15 minutes and is then diluted with additional water to a single strength concentration prior to use.

The daily doses of ubiquinone 10 and succinic acid for administration in accordance with this invention can be administered as single doses, or they can be divided and administered as a multiple-dose daily regimen. Thus, the doses of ubiquinone 10 and succinic acid may be administered 1 to 4 times a day until patient symptoms of fibromyalgia have subsided or are stabilized. Further, a staggered regimen, for example, one to three days of buccal/sublingual ubiquinone 10 and succinic acid treatments per week, can be used as an alternative to daily treatment, and for the purpose of defining this invention such intermittent or staggered daily regimen is considered to be equivalent to every day treatment and within the scope of this invention.

EXAMPLE 1

Preparation of Ubiquinone 10 and Succinic Acid-containing Liquid Solutions

Ubiquinone 10 is synthesized according to the procedure described in U.S. Pat. No. 4,070,244 incorporated herein by reference in its entirety. Succinic acid is purchased from Aldrich Chemical Company, Milwaukee, Wis. A ubiquinone 10 and succinic acid-containing liquid solution is prepared by first dissolving ubiquinone 10 and succinic acid in phosphate-buffered saline. To prepare a physiological phosphate-buffered saline solution for dissolution of the ubiquinone 10 and succinic acid, a concentrated (20×) solution of phosphate buffered saline (PBS) is diluted to obtain a 1× solution. The 20× PBS solution is prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The PBS solution is then sterilized by autoclaving at 15 pounds of pressure for 15 minutes and is diluted with additional sterile water to a 1× concentration prior to dissolution of the ubiquinone 10 and succinic acid. To prepare a dose form for intravenous administration, ubiquinone 10 and succinic acid are dissolved in 1× PBS at concentrations of 0.5 and 2 mg/ml, respectively, and the resulting solution (200 ml) is dispensed into sealable translucent plastic bags for use in intravenous administration of the compounds. These steps are performed under sterile conditions. Alternatively, ubiquinone 10 and succinic acid are dissolved in sterile 1× PBS at concentrations of 100 and 400 mg/ml, respectively, and 10 ml aliquots are dispensed, under sterile conditions, into glass vials which are then sealed with a rubber septum. Such dosage forms are useful for parenteral administration of the compounds by subcutaneous, intramuscular, intraperitoneal, and intradermal injection at approximately 1 ml per dose. The buffered aqueous solution of ubiquinone 10 and succinic acid is also used as a base for preparing other liquid formulations of the compounds. For example, a syrup is prepared by adding art-recognized caloric or non-caloric sweeteners, flavor oils, and pharmaceutically acceptable surfactants/dispersants to an aqueous solution of ubiquinone 10 and succinic acid. Such a syrup dosage form contains ubiquinone 10 and succinic acid at concentrations of 100 and 400 mg/ml, respectively, and is administered in 1 ml amounts. A ubiquinone 10 and succinic acid-containing spray is similarly formulated, but contains flavoring in an aqueous form, and a convenient means of delivering an aerosol spray is utilized.

EXAMPLE 2

Preparation of Ubiquinone 10 and Succinic Acid-containing Lozenges

Lozenges for use in accordance with this invention can be prepared by art-recognized techniques for forming compressed tablets. The ubiquinone 10 and succinic acid is dispersed on a compressible solid carrier and is formed into tablets each containing a predetermined amount of the active ingredients. For example, each lozenge may contain 100 mg of ubiquinone 10 and 400 mg of succinic acid, or, alternatively, 25 mg of ubiquinone 10 and 100 mg of succinic acid or any other therapeutically effective amounts. The solid carrier component for such tableting formulations can be a saliva-soluble solid, such as a cold water-soluble starch or a monosaccharide or disaccharide, so that the lozenge will readily dissolve in the mouth to release the contained ubiquinone 10 and succinic acid in saliva solution for contact with and absorption by the oral/pharyngeal mucosa when the lozenge is held in the mouth. A preferred solid carrier is dibasic calcium phosphate. The ubiquinone 10 and succinic acid is also optionally combined with any appropriate tableting aids such as a lubricant (e.g., magnesium-stearate), a binding agent, a wetting agent, or a disintegrant. The product is then shaped by art-recognized techniques into the desired delivery form. The pH of the formulations ranges from about 4 to about 8.5.

EXAMPLE 3

Preparation of Ubiquinone 10 and Succinic Acid-containing Tablets

Tablets for use in accordance with this invention can be prepared in a manner similar to that described in Example 2 for preparation of lozenges except that a saliva-soluble solid carrier for dissolution in the mouth is not required. The ubiquinone 10 and succinic acid may be presented as a powder, and suitable solid carrier components for tableting include manitol, microcrystalline cellulose, and carboxymethyl cellulose. A preferred solid carrier for use in accordance with the invention is dibasic calcium phosphate. Tablets may also be prepared by other art-recognized techniques for forming compressed tablets such as chewable vitamins.

EXAMPLE 4

Treatment of a Female Fibromyalgia Subject With Ubiquinone 10 and Succinic Acid Using a Single Daily Dose Regimen A 45 year old female subject presents with fatigue, dizziness, muscle cramps and pain, joint pain, headaches, and diminished sleep. The subject is examined, and is diagnosed as suffering from fibromyalgia by finding pain at 14 of 18 characteristic tender points when a finger pressure of about 4 kg is applied to the area. The subject is treated with ubiquinone 10 and succinic acid-containing lozenges by buccal administration, with each lozenge containing 25 mg of ubiquinone 10 and 100 mg of succinic acid, in four daily doses with food for one month. After 1 month of daily treatment with the ubiquinone 10 and succinic acid-containing lozenges, the subject's condition is improved with the dizziness, muscle and joint pain, and headaches diminished. Considerable improvement in physical activity and sleep is also observed. The subject is reexamined to determine the tender point index after treatment with ubiquinone 10 and succinic acid and pain is found at only 4 of the 18 characteristic tender points. The subject continues on the same treatment regimen and no side effects are observed.

EXAMPLE 5

Treatment of a Male Fibromyalgia Subject With Ubiquinone 10 and Succinic Acid

A 37 year old male subject presents with general fatigue, restlessness, muscle and joint pain, numbness, and abdominal cramps. The subject is examined, and is positively diagnosed as suffering from fibromyalgia by finding pain at 17 of 18 characteristic tender points when 4 kg of finger pressure is applied. The subject is treated with ubiquinone 10 and succinic acid by parenteral administration of a ubiquinone 10 and succinic acid-containing buffered liquid solution. The liquid dose formulation is administered so that the subject receives a dose of 100 mg per day of ubiquinone 10 and 400 mg per day of succinic acid with food for 14 days. The subject is reexamined to determine the subject's tender point index after 14 days and pain is found at only 6 of the 18 characteristic tender points. Considerable improvement in the subject's muscle and joint pain and abdominal pain are observed and the subject indicates that he feels better physically and mentally. The subject continues treatment on the same treatment regimen as described in Example 4 and his symptoms continue to subside. The subject does not complain of any side effects.

EXAMPLE 6

Treatment of a Female Fibrobyalgia Subject With Ubiquinone 10 and Succinic Acid Using a Multi-dose Daily Regimen A 29 year old female subject presents with muscle cramps, joint pain, stiffness, and general fatigue. The subject also complains of sleep abnormalities. The subject is examined, and is positively diagnosed as suffering from fibromyalgia by finding pain at 15 of 18 characteristic tender points when 4 kg of finger pressure is applied to the area. The subject is treated with ubiquinone 10 and succinic acid by oral ingestion of a ubiquinone 10 and succinic-containing syrup wherein the subject swallows the syrup upon administration and does not hold the syrup in the mouth for a period of time before swallowing. Each dose of this liquid formulation contains 25 mg of ubiquinone 10 and 100 mg of succinic acid, and is administered in 4 daily doses with food for a period of 3 weeks. The subject is reexamined after 3 weeks and pain is found at only 2 of the 18 characteristic tender points. Considerable improvement in the subject's muscle and joint pain are observed and the subject indicates that she feels better physically. The subject continues on the same treatment regimen and does not complain of any side effects.

EXAMPLE 7

Treatment of a Female Fibromyalgia Subject With Ubiquinone 10 and Succinic Acid

A 48 year old female was positively diagnosed with fibromyalgia. The subject found no relief for her pain after receiving standard medical treatment. The subject began treatment with 50 mg of ubiquinone 10 and 200 mg of succinic acid in capsule form twice daily with food. The subject experienced dramatic relief of her symptoms by the fifth day after treatment commenced with almost complete cessation of symptoms by the fourteenth day after treatment began. She improved further over a six week period until she became asymptomatic, and continues on the same treatment regimen.

EXAMPLE 8

Treatment of a Female Fibromyalgia Subject With Ubiquinone 10 and Succinic Acid

A 40 year old female was diagnosed with fibromyalgia and began treatment with 100 mg of ubiquinone 10 and 400 mg of succinic acid in a single daily dose in capsule form with food. The subject experienced some stomach upset with 400 mg of succinic and her succinic acid dose was reduced to 200 mg per day. The subject experienced dramatic relief from her pain and other symptoms and became asymptomatic within 30 days. She continues on the same treatment regimen with no recurrence of symptoms.

EXAMPLE 9

Treatment of a Female Fibromyalgia Subject With Ubiquinone 10 and Succinic Acid

A 32 year old patient was diagnosed with fibromyalgia and began treatment with ubiquinone 10 and succinic acid three months later. The subject was treated with 100 mg of ubiquinone 10 and 200 mg of succinic acid twice daily in capsule form with food. The subject noted some relief from her symptoms by the end of the first week of treatment. She continued to improve and complete cessation of symptoms was observed by the end of thirty days. She continues on the same treatment regimen and has no reoccurence of symptoms.

EXAMPLE 10

Treatment of a Female Lupus Erythematosus Subject With Ubiquinone 10 and Succinic Acid A 60 year old female diagnosed with lupus found no satisfactory results with standard medical treatment. The subject began treatment with 100 mg of ubiquinone 10 and 400 mg of succinic acid in capsule form with food in two daily doses. The subject experienced remission of her symptoms within about two weeks after treatment began and continues on the same treatment regimen.

EXAMPLE 11

Treatment of a Female Lupus Erythematosus Subject With Ubiquinone 10 and Succinic Acid A 65 year old female was diagnosed with lupus erythematosus and was treated using the same regimen as described in Example 10. The subject experienced complete remission of symptoms in about 2 weeks, and continues on the same treatment regimen.

EXAMPLE 12

Treatment of a Female Subject With Chronic Fatigue Syndrome With Ubiquinone 10 and Succinic Acid A 40 year old female subject was diagnosed with chronic fatigue syndrome and was sent to numerous specialists without improvement. The subject began treatment with 100 mg of ubiquinone 10 and 400 mg of succinic acid in capsule form with food once daily. The subject's symptoms subsided within 3 days and she was asymptomatic within two weeks, and continues on the same treatment regimen without recurrence of symptoms.

EXAMPLE 13

Treatment of a Male Diabetes Subject With Ubiquinone 10 and Succinic Acid

A 62 year old male subject was diagnosed with diabetes and had high blood sugar levels even with medical treatment. The subject began treatment with 50 mg of ubiquinone 10 and 200 mg of succinic acid in capsule form twice daily with food. The subject's blood sugar level was lowered to 112 and has been maintained at that level since the ubiquinone 10 and succinic acid treatment was initiated. The subject continues on the same treatment regimen.

EXAMPLE 14

Treatment of a Male Diabetes Subject With Ubiquinone 10 and Succinic Acid

A 60 year old male subject was diagnosed with diabetes and had high blood sugar levels even with medical treatment. The subject began treatment with 50 mg of ubiquinone 10 and 200 mg of succinic acid in capsule form twice daily with food. The subject's blood sugar level was lowered and swelling in his feet subsided. The subject continues on the same treatment regimen.

EXAMPLE 15

Treatment of a Male Diabetes Subject With Ubiquinone 10 and Succinic Acid

A 70 year old male subject was diagnosed with diabetes. He began treatment with 100 mg of ubiquinone 10 and 400 mg of succinic acid with food in a single daily dose in capsule form. The treatment with ubiquinone 10 and succinic acid has lowered and controlled the subject's blood glucose level and he continues on the same treatment regimen.

What is claimed is:

1. A method for treating a human patient suffering from fibromyalgia to produce a therapeutic response in said patient, said method comprising the step of administering to the patient ubiquinone 10 and succinic acid each at a dose of about 5 to about 500 mg/70 kg patient.

2. The method of claim 1 wherein the ubiquinone 10 and the succinic acid are each administered at a dose of about 50 to about 400 mg/70 kg patient.

3. The method of claim 1 wherein the ubiquinone 10 and the succinic acid are each administered at a dose of about 50 to about 200 mg/70 kg patient.

4. The method of claim 1 wherein the ubiquinone 10 and the succinic acid are formulated in combination in a pharmaceutically acceptable solid dosage form.

5. The method of claim 1 wherein the ubiquinone 10 and the succinic acid are formulated in combination in a pharmaceutically acceptable liquid dosage form.

6. The method of claim 4 wherein the solid dosage form is a saliva-soluble solid dosage form of said combination which is administered by being introduced into the mouth of the patient and held in the mouth for a period of time sufficient to dissolve in saliva in the patient's mouth to form a saliva solution comprising ubiquinone 10 and succinic acid.

7. The method of claim 6 wherein the solid dosage form is a lozenge.

8. The method of claim 1 wherein the ubiquinone 10 and the succinic acid are administered by oral ingestion.

9. The method of claim 1 wherein the ubiquinone 10 and the succinic acid are administered bucally.

10. The method of claim 1 wherein the ubiquinone 10 and the succinic acid are administered sublingually.

11. The method of claim 1 wherein the ubiquinone 10 and the succinic acid are administered parenterally.

12. The method of claim 1 wherein the dose of ubiquinone 10 and succinic acid is administered 1 to 4 times a day until the patient's symptoms of fibromyalgia have subsided.

* * * * *